United States Patent [19]

O'Neill

[11] Patent Number: 5,521,220
[45] Date of Patent: May 28, 1996

[54] ACYCLIC ETHYLENEDIAMINE DERIVATIVES

[75] Inventor: Brian T. O'Neill, Westbrook, Conn.

[73] Assignee: Pfizer Inc., New York, N.Y.

[21] Appl. No.: 240,657

[22] PCT Filed: Sep. 18, 1992

[86] PCT No.: PCT/US92/07730

§ 371 Date: Jul. 20, 1994

§ 102(e) Date: Jul. 20, 1994

[87] PCT Pub. No.: WO93/10073

PCT Pub. Date: May 27, 1993

Related U.S. Application Data

[63] Continuation-in-part of Ser. No. 790,934, Nov. 12, 1991, abandoned.

[51] Int. Cl.⁶ .......................... A61K 31/13; C07C 211/27
[52] U.S. Cl. .......... 514/649; 514/647; 514/648; 514/659; 564/306; 564/317; 564/367; 564/370; 564/372; 564/452
[58] Field of Search .................... 564/306, 317, 564/370, 367, 372, 452; 514/648, 649, 647, 659

[56] References Cited

U.S. PATENT DOCUMENTS

| | | | |
|---|---|---|---|
| 2,514,380 | 7/1950 | Duschinsky | 564/369 |
| 2,634,293 | 4/1953 | Kyrides | 564/369 |
| 2,746,959 | 5/1956 | Bruce et al. | 564/370 |
| 2,876,236 | 3/1959 | Szabo | 564/445 |
| 5,138,060 | 8/1994 | Godek | 546/133 |

FOREIGN PATENT DOCUMENTS

| | | |
|---|---|---|
| 973694 | 2/1951 | France . |
| 1173833 | 12/1969 | United Kingdom . |
| 90/05729 | 5/1990 | WIPO . |
| 91/18899 | 12/1991 | WIPO . |
| 91/18878 | 12/1991 | WIPO . |
| 92/01688 | 2/1992 | WIPO . |
| 92/06079 | 4/1992 | WIPO . |
| 92/12151 | 7/1992 | WIPO . |

OTHER PUBLICATIONS

Duschinsky et al., J.A.C.S., 69, p. 3150 (1947).
Funke et al., Bull. Soc. Chim. Francais, pp. 241–245 (1949).
Mehotra et al., Indian J. of Chem., 15B, pp. 1106–1109 (1977).
Gainsford et al., J. of Chem. Soc., Chem. Comm., pp. 857–858 (1978).
Cortes et al., J. Org. Chem. 48, pp. 2246–2254 (1983).
Toja et al., Heterocycles, 26(8), pp. 2129–2138 (1987).
Tanaka et al., Tet. Letters, 29(31), pp. 3811–3814 (1988).
Fenton et al. I, Inorg. Chim. Acta., 148(1) pp. 37–44 (1988).
Fenton et al. II, Inorg. Chim. Acta., 182(1), pp. 59–66 (1991).
Sivov et al., Deposited Doc., VINIT 3167-81, 210–12 (1981).
Lehmann et al., J. of Pharmacology & Experimental Therapeutics, 91(1), pp. 114–125 (1948).

*Primary Examiner*—Bernard Dentz
*Attorney, Agent, or Firm*—Peter C. Richardson; Paul H. Ginsburg; Seymour G. Bekelnitzky

[57] ABSTRACT

The present invention relates to novel acyclic ethylenediamine derivatives of nitrogen containing heterocyclic compounds, and specifically, to compounds of the formula

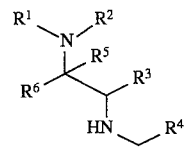

wherein $R^1$, $R^2$, $R^3$, $R^4$, $R^5$ and $R^6$ are defined as in the specification. It also relates to novel intermediates used in the synthesis of such derivatives.

Compounds of the formula I and their pharmaceutically acceptable salts are useful in the treatment of inflammatory and central nervous system disorders, as well as other disorders.

11 Claims, No Drawings

ACYCLIC ETHYLENEDIAMINE DERIVATIVES

This application is a 371 of PCT/US 92/07730 filed Sep. 18, 1992, which is a continuation-in-part of U.S. Ser. No. 790,934, which was filed on Nov. 12, 1991, now abandoned.

BACKGROUND OF THE INVENTION

The present invention relates to novel acyclic ethylenediamine derivatives, pharmaceutical compositions comprising such compounds and the use of such compounds in the treatment and prevention of inflammatory and central nervous system disorders, as well as several other disorders. The pharmaceutically active compounds of this invention are substance P receptor antagonists. This invention also relates to novel intermediates used in the synthesis of such substance P receptor antagonists.

Substance P is a naturally occurring undecapeptide belonging to the tachykinin family of peptides, the latter being named because of their prompt stimulatory action on smooth muscle tissue. More specifically, substance P is a pharmacologically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine (see B. E. B. Sandberg et al., *Journal of Medicinal Chemistry*, 25, 1009 (1982)), as well as in central nervous system disorders such as anxiety and schizophrenia, in respiratory and inflammatory diseases such as asthma and rheumatoid arthritis, respectively, in rheumatic diseases such as fibrositis, and in gastrointestinal disorders and diseases of the GI tract such as ulcerative colitis and Crohn's disease, etc. (see D. Regoli in "Trends in Cluster Headache," edited by F. Sicuteri et al., Elsevier Scientific Publishers, Amsterdam, pp. 85–95 (1987)).

Quinuclidine, piperidine, azanorbornane derivatives and related compounds that exhibit activity as substance P receptor antagonists are referred to in U.S. patent application Ser. No. 566,338 filed Nov. 20, 1989, U.S. patent application Ser. No. 724,268, filed Jul. 1, 1991, PCT Patent Application PCT/US 91/02853, filed Apr. 25, 1991, PCT Patent Application PCT/US 91/03369, filed May 14, 1991, PCT Patent Application PCT/US 91/05776, filed Aug. 20, 1991, PCT Patent Application PCT/US 92/00113, filed Jan. 17, 1992, PCT Patent Application PCT/US 92/03571, filed May 5, 1992, PCT Patent Application PCT/US 92/03317, filed Apr. 28, 1992, PCT Patent Application PCT/US 92/04697, filed Jun. 11, 1992, U.S. patent application Ser. No. 766,488, filed Sep. 26, 1991, U.S. patent application Ser. No. 790,934, filed Nov. 12, 1991, PCT Patent Application PCT/US 92/04002, filed May 19, 1992, and Japanese Patent Application No. 065337/92, filed Mar. 23, 1992.

SUMMARY OF THE INVENTION

The present invention relates to compounds of the formula

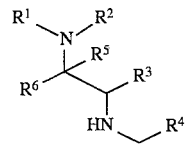

I wherein $R^1$ is hydrogen, $(C_1-C_8)$ alkyl, a saturated $(C_6-C_{10})$ carbocyclic ring system containing two fused rings, a saturated $(C_6-C_{10})$ carbocyclic bridged ring system containing two rings, or benzyl wherein the phenyl moiety of said benzyl may optionally be substituted with one or more substituents independently selected from halo, $(C_1-C_6)$ alkyl optionally substituted with from one to three fluorine atoms and $(C_1-C_8)$ alkoxy optionally substituted with from one to three fluorine atoms;

$R^2$ is hydrogen, benzyl or a group of the formula

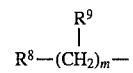

wherein m is an integer from zero to twelve, and any one of the carbon-carbon single bonds of $(CH_2)_m$, wherein both carbon atoms of such bond are bonded to each other and to another carbon atom of the $(CH_2)_m$ chain, may optionally be replaced by a carbon-carbon double or triple bond, and any one of the carbon atoms of $(CH_2)_m$ may optionally be substituted with $R^9$;

$R^8$ and $R^9$ are independently selected from hydrogen, hydroxy, halo, amino, carboxy, carboxy$(C_1-C_6)$alkyl, $(C_1-C_6)$alkylamino, di-$(C_1-C_6)$alkylamino, $(C_1-C_6)$alkoxy,

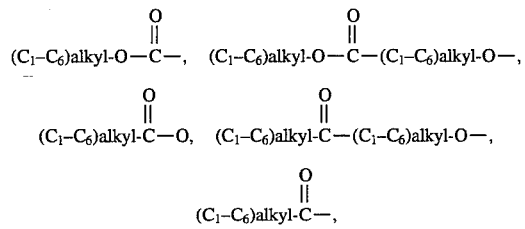

$(C_1-C_6)$ straight or branched alkyl, $(C_3-C_7)$ cycloalkyl wherein one of the carbon atoms may optionally be replaced by nitrogen, oxygen or sulfur; aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; phenyl-$(C_2-C_6)$alkyl, benzhydryl and benzyl, wherein each of said aryl and heteroaryl groups and the phenyl moieties of said benzyl, phenyl-$(C_2-C_6)$alkyl and benzhydryl may optionally be substituted with one or two substituents independently selected from halo, nitro, $(C_1-C_6)$alkyl optionally substituted with from one to three fluorine atoms, $(C_1-C_6)$alkoxy optionally substituted with from one to three fluorine atoms, amino, $(C_1-C_6)$-alkylamino,

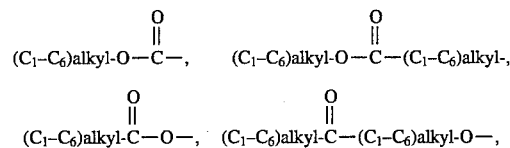

-continued

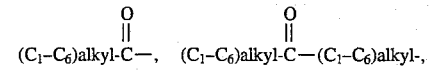

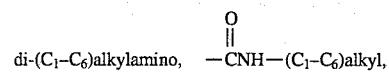

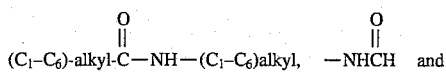

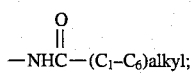

and wherein one of the phenyl moieties of said benzhydryl may optionally be replaced by naphthyl, thienyl, furyl or pyridyl;

or $R^1$ and $R^2$, together with the nitrogen to which they are attached, form a saturated or unsaturated monocyclic ring containing from three to eight carbon atoms, a fused bicyclic ring containing from six to ten carbon atoms, or a saturated bridged ring system, containing from six to ten carbon atoms;

$R^4$ is aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; and cycloalkyl having from three to seven carbon atoms wherein one of said carbon atoms may optionally be replaced by nitrogen, oxygen or sulfur; wherein each of said aryl and heteroaryl groups may optionally be substituted with one or more substituents, and said $(C_3-C_7)$ cycloalkyl may optionally be substituted with one, two or three substituents, each of said substituents being independently selected from halo, nitro, $(C_1-C_6)$ alkyl optionally substituted with from one to three fluorine atoms, $(C_1-C_6)$ alkoxy optionally substituted with from one to three fluorine atoms, phenyl, amino, $((C_1-C_6)$ alkylamino,

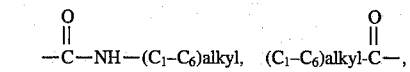

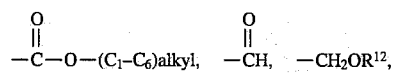

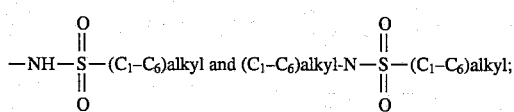

$R^3$ is hydrogen, $(C_3-C_8)$cycloalkyl, $(C_1-C_6)$ straight or branched alkyl or phenyl optionally substituted with one or more substituents independently selected from halo, $(C_1-C_6)$alkyl optionally substituted with from one to three fluorine atoms, and $(C_1-C_6)$alkoxy optionally substituted with from one to three fluorine atoms;

$R^5$ is hydrogen, $(C_1-C_6)$alkyl, or phenyl optionally substituted with one or more substituents independently selected from halo, $(C_1-C_6)$alkyl optionally substituted with from one to three fluorine atoms and $(C_1-C_6)$alkoxy optionally substituted with from one to three fluorine atoms;

$R^6$ is selected from hydrogen, $(C_1-C_6)$ straight or branched alkyl, $(C_3-C_7)$ cycloalkyl wherein one of the carbon atoms may optionally be replaced by nitrogen, oxygen or sulfur; aryl selected from phenyl, biphenyl, indanyl and naphthyl; heteroaryl selected from thienyl, furyl, pyridyl, thiazolyl, isothiazolyl, oxazolyl, isoxazolyl, triaz-olyl, tetrazolyl and quinolyl; phenyl $(C_2-C_6)$ alkyl, benzhydryl and benzyl, wherein each of said aryl and heteroaryl groups and the phenyl moieties of said benzyl, phenyl $(C_2-C_6)$ alkyl and benzhydryl may optionally be substituted with one or more substituents independently selected from halo, nitro, $(C_1-C_6)$ alkyl optionally substituted with from one to three fluorine atoms, $((C_1-C_6)$ alkoxy, trifluoromethyl, amino, trihaloalkoxy (e.g., trifluoromethoxy), $(C_1-C_6)$alkylamino,

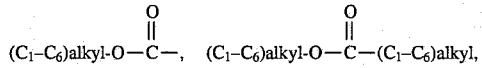

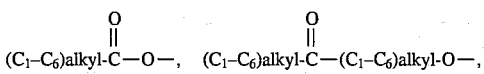

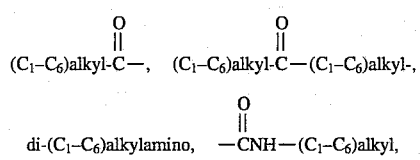

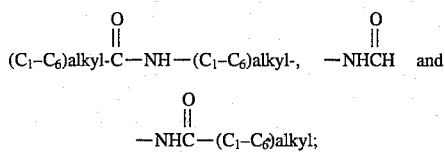

and wherein one of the phenyl moieties of said benzhydryl may optionally be replaced by naphthyl, thienyl, furyl or pyridyl; and $R^{12}$ is hydrogen, $(C_1-C_3)$alkyl or phenyl.

Preferred compounds of the formula I include those wherein $R^2$ is hydrogen, or $R^2$ and $R^1$, together with the nitrogen to which they are attached, form a monocyclic ring containing five to seven carbon atoms; $R^3$ is hydrogen, methyl or phenyl; $R^5$ is hydrogen; $R^4$ :is phenyl or indanyl, wherein said phenyl or indanyl may optionally be substituted with from one to three substituents independently selected from halo, nitro, $(C_1-C_6)$ alkyl optionally substituted with from one to three fluorine atoms, $(C_1-C_6)$ alkoxy, trihaloalkoxy (e.g., trifluoromethoxy), $(C_1-C_6)$ alkylamino, —C(O)NH—$(C_1-C_8)$alkyl, $(C_1-C_6)$alkyl—C(O)—, —C(O)—O—$(C_1-C_6)$alkyl, —C(O)H, —CH$_2$OR$^{13}$, —NH$(C_1-C_6)$alkyl, —NHC(O)H, —NHC(O)—$(C_1-C_6)$alkyl, —NHSO$_2$$(C_1-C_6)$alkyl and $((C_1-C_6)$alkyl—N—SO$_2$—$(C_1-C_6)$alkyl; and $R^6$ is phenyl.

Particularly preferred compounds of the formula I are those wherein $R^1$ is alkyl, $R^6$ is unsubstituted phenyl, $R^4$ is a monosubstituted or disubstituted aryl group that is substituted at the C-2 position with an alkoxy group or substituted at the C-5 position with an alkyl, alkoxy or trihaloalkoxy group, or substituted in such manner at both C-2 and C-5 positions (i.e., with an alkoxy group at the C-2 position and an alkyl, alkoxy or trihaloalkoxy group at the C-5 position), and each of $R^2$, $R^3$ and $R^5$ is hydrogen.

Examples of preferred compounds of the formula I include:

1-N-cyclohexyl-1-phenyl-2-N'-[(2-methoxyphenyl)methyl]-1,2-ethanediamine;

1-N-cyclohexyl-1-phenyl-2-N'-[(2-methoxy-5-trifluoromethoxyphenyl)methyl]-1,2-ethanediamine;

1-N-pyrrolidyl-1-phenyl-2-N'-[(2-methoxyphenyl)methyl]-1,2-ethanediamine;

1-N-methyl-1-phenyl-2-N'-[(2-methoxyphenyl)methyl]-1,2-ethanediamine;

1-N-cyclopentyl-1-phenyl-2-N'-[(2-methoxyphenyl)methyl]-1,2-ethanediamine;

1-N-propyl-1-phenyl-2-N'-[(2 -methoxyphenyl)methyl]-1,2-ethanediamine;

1-N-phenylmethyl-1-phenyl-2-N'-[(2 -methoxyphenyl)methyl]-1,2-ethanediamine;

1-N-cyclooctyl-1-phenyl-2-N'-[(2 -methoxyphenyl)methyl]-1,2-ethanediamine;

1-N-cyclobutyl-1-phenyl-2-N'-[(2 -methoxyphenyl)methyl]-1,2-ethanediamine;

1-N-(2-adamantyl)-1-phenyl-2-N'-[(2 -methoxyphenyl)methyl]-1,2-ethanediamine;

1-N-(1,1-dimethylethyl)-1-phenyl-2-N'-[(2-methoxyphenyl)methyl]-1,2-ethanediamine;

1-N-cyclopropyl-1-phenyl-2-N'-[(2 -methoxyphenyl)methyl]-1,2-ethanediamine;

1-N-isopropyl-1-phenyl-2-N'-[(2 -methoxyphenyl)methyl]-1,2-ethanediamine;

1-N-(1-phenylethyl)-1-phenyl-2-N'-[(2 -methoxyphenyl)methyl]-1,2 -ethanediamine;

1-N-(2-norbornyl)-1-phenyl-2-N'-[(2 -methoxyphenyl)methyl]-1,2-ethanediamine;

1-N-cyclohexyl-1-phenyl-2-N'-[(2 -methoxy-5-tertbutylphenyl)methyl]-1,2-ethanediamine;

1-N-cyclohexyl-1-phenyl-2-N'-[(2 -methoxy-5-isopropylphenyl)methyl]-1,2-ethanediamine;

1-N-cyclohexyl-1-phenyl-2-N'-[(2 -methoxy-4,5-dimethylphenyl)methyl]-1,2 -ethanediamine; and 1-N-cyclohexyl-1-N-(6-hydroxyhexyl)-1 -phenyl-2-N'-[(2-methoxyphenyl)methyl]-1,2 -ethanediamine.

Other compounds of the formula I include:

1-N-phenyl-1-phenyl-2-N'-[(2 -methoxyphenyl)methyl]-1,2-ethanediamine

1-N-(2-aza-bicyclo[4.4.0]decane)-1 -phenyl-2-N'-[(2-methoxyphenyl)methyl]-1,2-ethanediamine;

1,1-diphenyl-2-N'-[(2-methoxyphenyl)methyl]-1,2-ethanediamine;

1,1-diphenyl-2-N'-[(2,5 -dimethoxyphenyl)methyl]-1,2-ethanediamine;

1,1-diphenyl-2-N'-[(2,4 -dimethoxyphenyl)methyl]-1,2-ethanediamine;

1-N-cyclohexyl-1-N-(6-n-hexanol)-1 -phenyl-2-N'-[(2-methoxyphenyl)methyl]-1,2 -ethanediamine;

1-N-cyclohexyl-1-N-(3-phenylpropyl)-1 -phenyl-2-N'-[(2-methoxyphenyl)methyl]-1,2-ethanediamine;

3,3-diphenyl-2-N-cyclopentyl-1-N'-[(2 -methoxyphenyl)methyl]-1,2-propanediamine;

1-N-(2-phenylethyl)-1-(3,4 -methylenedioxyphenyl)-2-N'-2-methoxyphenyl)methyl]-1,2-ethanediamine;

1-N-cyclopentyl-1-(2-napthyl)-2 -N'-[(2-methoxyphenyl)methyl]-1,2-ethanediamine;

1-N-cyclohexyl-1-cyclohexyl-1-N'-[(2 -methoxyphenyl)methyl]-1,2-ethanediamine;

1-cyclohexylamino-1-phenyl-2-[(2 -methoxyphenyl)methylamino]propane;

1-N-pyrrolidyl-1-phenyl-2-[(2 -methoxyphenyl)methylamino]propane;

1-N-piperidyl-1-phenyl-2-[(2 -methoxyphenyl)methylamino]propane;

1-cyclopentylamino-1-phenyl-2-[(2 -methoxyphenyl)methylamino]propane;

1-cyclooctylamino-1-phenyl-2-[(2 -methoxyphenyl)methylamino]propane;

1-propylamino-1-phenyl-2-[(2 -methoxyphenyl)methylamino]propane;

1-amino-1-phenyl-2-[(2 -methoxyphenyl)methylamino]-3-methoxypropane;

1-methylamino-1-phenyl-2-[(2 -methoxyphenyl)methylamino]-3-methoxypropane;

1-cycloheptylamino-1-phenyl-2-[(2 -methoxyphenyl)methylamino]propane;

1-amino-1-phenyl-2-[(2 -methoxyphenyl)methylamino]propane;

1-(4-pyranyl)amino-1-phenyl-2 -[(2-methoxyphenyl)methylamino]propane;

1-N-cyclopentyl-1-phenyl-2-N'-[(2 -methoxy-5-tertbutylphenyl)methyl]-1,2-ethanediamine;

1-N-methyl-1-phenyl-2-N'-[(2 -methoxy-5-tertbutylphenyl)methyl]-1,2-ethanediamine;

1-N-cyclopentyl-1-phenyl-2-N'-[(2 -methoxy-5-isopropylphenyl)methyl]-1,2-ethanediamine;

1-N-methyl-1-phenyl-2-N'-[(2 -methoxy-5-isopropylphenyl)methyl]-1,2-ethanediamine;

1-N-cyclopentyl-1-phenyl-2-N'-[(2 -methoxy-4,5-dimethylphenyl)methyl]-1,2-ethanediamine;

1-N-methyl-1-phenyl-2-N'-[(2 -methoxy-4,5-dimethylphenyl)methyl]-1,2-ethanediamine;

1-N-cyclohexyl-1-phenyl-2-N'-[(2 -methoxy-5-(methylamino-N-methanesulfonamide)phenyl)methyl]-1,2-ethanediamine;

1-N-methyl-1-phenyl-2-N'-[(2 -methoxy-5-(methylamino-N-methanesulfonamide)phenyl)methyl]-1,2-ethanediamine;

1-N-cyclopentyl-1-phenyl-2-N'-[(2 -methoxy-5-(methylamino-N-methanesulfonamide)phenyl)methyl]-1,2ethanediamine;

1-N-cyclohexyl-1-phenyl-2-N'-[(2 -methoxy-5-(2-propylamino-N-methanesulfonamide)phenyl)methyl]-1,2ethanediamine;

1-N-methyl-1-phenyl-2-N'-[(2 -methoxy-5-(2-propylamino-N-methanesulfonamide)phenyl)methyl]-1,2-ethanediamine; and 1-N-cyclopentyl-1-phenyl-2-N'-[(2 -methoxy-5-(2-propylamino-N-methanesulfonamide)phenyl)methyl]-1,2-ethanediamine.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The present invention also relates to compounds of the formula

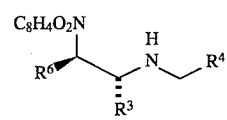

IX wherein $R^3$, $R^4$ and $R^6$ are defined as for formula I. These compounds are useful as intermediates in the synthesis of compounds of the formula I.

The term "halo", as used herein, unless otherwise indicated, includes chloro, fluoro, bromo and iodo.

The term "alkyl", as used herein, unless otherwise indicated, includes saturated monovalent hydrocarbon radicals having straight, branched or cyclic moieties or combinations thereof.

The term "alkoxy," as used herein, includes -O-alkyl groups wherein "alkyl" is defined as above.

The term "one or more substituents," as used herein, includes from one to the maximum number of substituents possible based on the number of available bonding sites.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in treating or preventing such condition, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, coliris, psychosis, pain, allergies such as eczema and thiniris, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in treating or preventing such condition.

The present invention also relates to a pharmaceutical composition for antagonizing the effects of substance P in a mammal, including a human, comprising a substance P antagonizing amount of a compound of the formula I, or a pharmaceutically acceptable salt thereof, and a pharmaceutically acceptable carrier.

The present invention also relates to a method of antagonizing the effects of substance P in a mammal, including a human, comprising administering to said mammal a substance P antagonizing amount of a compound of the formula I, or a pharmaceutically acceptable salt thereof.

The present invention also relates to a pharmaceutical composition for treating or preventing a disorder in a mammal, including a human, resulting from an excess of substance P, comprising a substance P antagonizing amount of a compound of the formula I, or a pharmaceutically acceptable salt thereof, and a pharmaceutically acceptable carrier.

The present invention also relates to a method of treating or preventing a disorder in a mammal, including a human, resulting from an excess of substance P, comprising administering to said mammal a substance P antagonizing amount of a compound of the formula I, or a pharmaceutically acceptable salt thereof.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in treating or preventing such disorder, and a pharmaceutically acceptable carrier.

The present invention also relates to a method of treating or preventing a disorder in mammal, including a human, the treatment or prevention, of which is effected or facilitated by a decrease in substance P mediated neurotransmission, comprising administering to said mammal an amount of a compound of the formula I, or a pharmaceutically acceptable salt thereof, effective in treating or preventing such disorder.

The compounds of the formulae I and IX have chiral centers and therefore exist in different enantiomeric forms. This invention relates to all optical isomers and all stereoisomers of compounds of the formulae I and IX, and mixtures thereof.

In addition to their utility as substance P receptor antagonists, the novel optically active compounds of the formula I are also useful as starting materials in the preparation of the corresponding racemic mixture and opposite enantiomer.

Formulae I and IX above include compounds identical to those depicted but for the fact that one or more hydrogen, nitrogen or carbon atoms are replaced by isotopes thereof (e.g., tritium, nitrogen-15, carbon-14 or carbon-11 isotopes thereof). Such compounds are useful as research and diagnostic tools in metabolism pharmokinetic studies and in binding assays. Specific applications in research include radioligand binding assays, autoradiography studies and in vivo binding studies, while specific applications in the diagnostic area include studies of the substance P receptor in the human brain in in vivo binding in the relevant tissues for inflammation, e.g. immune-type cells or cells that are directly involved in inflammatory bowel disorders and the like.

DETAILED DESCRIPTION OF THE INVENTION

The compounds of the formula I may be prepared as described in the following reaction schemes and discussion. Unless otherwise indicated $R^1$, $R^2$, $R^3$, $R^4$, $R^5$, $R^6$, $R^7$, $R^8$, $R^9$, $R^{10}$, $R^{11}$, $R^{12}$ and $R^{13}$, and structural formulae I and IX in the reaction schemes and discussion that follow are defined as above.

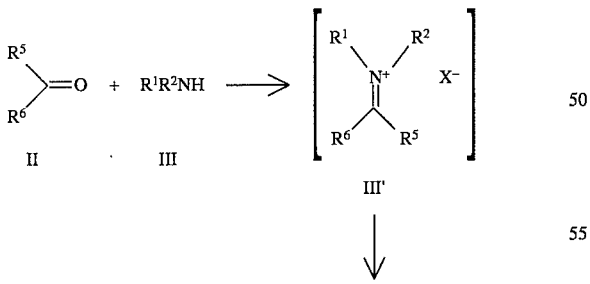

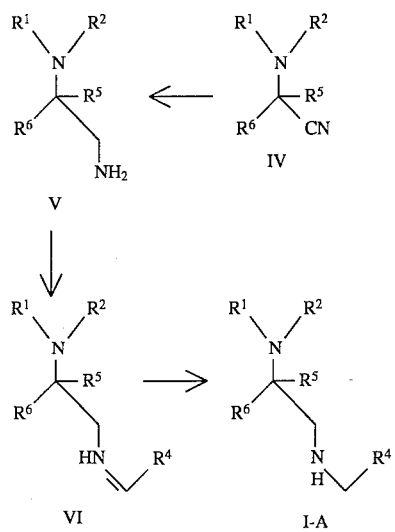

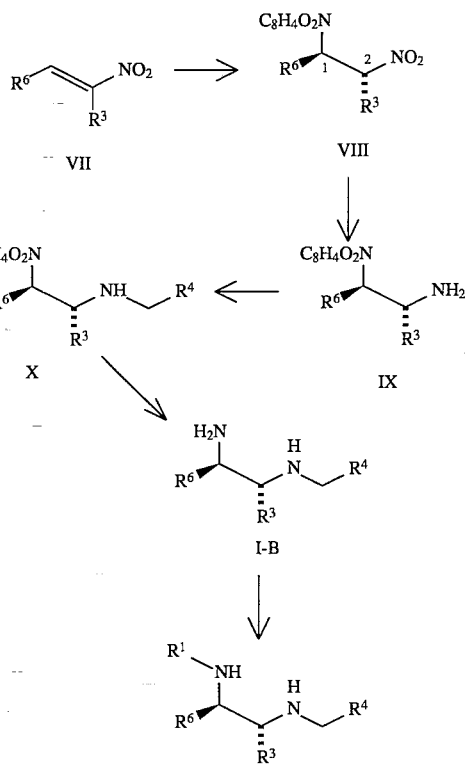

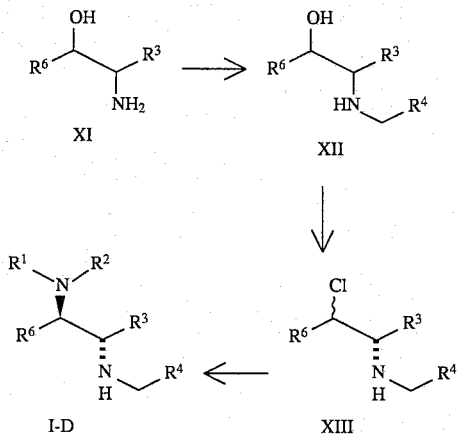

Scheme 3

Scheme 1 illustrates the preparation of compounds of the formula I.

Referring to scheme 1, a compound of the formula II is reacted with a compound of the formula III and a cyanide salt (e.g., potassium cyanide, sodium cyanide or trimethylsilyl cyanide) to yield the corresponding compound of formula IV. The cyanide salt, which is preferably potassium cyanide, is added last. The reaction is typically conducted in the presence of acid catalyst in an inert aqueous solvent such as methanol/water, tetrahydrofuran (THF)/water or acetonitrile/water, at a temperature from about 0° C. to about 40° C. It is preferably conducted in methanol/water at about room temperature. Acid catalysts that may be used include sodium bisulfite, potassium bisulfite, sodium biphosphate, acetic acid and hydrochloric acid. Sodium bisulfite is preferred. When trimethylsilyl cyanide is used, however, the reaction is preferably carried out neat or in THF, either in the absence of a catalyst or using zinc iodide as a catalyst.

The above reaction proceeds via an intermediate of the formula III' which is formed in situ. Alternatively, the intermediate may be formed in a separate step, isolated, and then reacted with a cyanide salt to form the corresponding compound of formula IV. This procedure is preferably carried out by reacting the compounds formula II and III under dehydrating conditions (e.g. in the presence of a titanium chloride catalyst or a dehydrating agent or using a Dean Stark trap) at a temperature from about 0° C. to about 40° C. Suitable solvents include benzene, toluene, methylene chloride and chloroform.

Reduction of the resulting nitrile having formula IV produces the corresponding diamine of formula V. The reduction is generally accomplished using diisobutylaluminum hydride, borane-THF, dimethylsulfide, lithium aluminum hydride or aluminum hydride, preferably diisobutylaluminum hydride. Suitable solvents include nonpolar solvents such as toluene, hexanes, petroleum ether and xylene. Toluene is preferred. The reaction temperature may range from about −78° C. to about 0° C., and is preferably between about −26° C. and 1° C.

The compound of formula V formed in the above step is then reacted with a compound of the formula $$\overset{O}{\underset{\|}{R^4CH}}$$

to produce the corresponding compound of formula VI. This reaction is generally carried out in an inert solvent such as benzene, toluene or another solvent that separates water (e.g., using a Dean-Stark trap), or in an inert solvent such as THF or methylene chloride in the presence of a drying agent (e.g., using molecular sieves). Suitable temperatures for this reaction range from about 25° C. to about 111° C. The reflux temperature of the solvent is preferred.

The resulting imine of formula VI may be converted to the corresponding compound of the formula I-A by reacting it with a reducing agent. Suitable reducing agents include sodium borohydride, hydrogen and a metal catalyst, sodium triacetoxyborohydride, sodium cyanoborohydride, zinc and hydrochloric acid, and formic acid. Sodium triacetoxyborohydride is preferred. This reduction is usually conducted in an inert solvent such as dichloroethane (DCE), dichloromethane (DCM), THF, methylene chloride, a lower alcohol, chloroform or acetic acid, preferably acetic acid, at a temperature from about −20° C. to about 60° C., preferably about room temperature.

Alternatively and preferably, reactions V→VI→I-A described above are carried out as one step without isolating the imine of formula VI. This procedure is illustrated in Example IC.

Scheme 2 illustrates the synthesis of compounds of the formula I wherein $R^1$, $R^2$ and $R^5$ are hydrogen having the depicted relative stereochemistry, i.e., the 1-(R,S)-2-(R,S) configuration as defined by the Cahn-Ingold-Prelog system (hereinafter referred to as compounds of the formula I-B), and compounds of the formula I wherein $R^1$ is $(C_1-C_8)$ alkyl, $R^5$ and $R^2$ are hydrogen, having the depicted relative stereochemistry, i.e., 1-(R,S)-2-(R,S) configuration as defined by the Cahn-Ingold-Prelog system (hereinafter referred to as compounds of the formula I-C). For convenience, only one enantiomer is depicted in scheme 2 for each of formulae VIII, IX, X, I-B and I-C. However, the procedure illustrated in scheme 2 applies to both enantiomers of these compounds.

Referring to scheme 2, a compound of the formula VII is reacted with phthalimide in the presence of a base. Generally, a reaction inert solvent such as THF or a lower alcohol is used. Examples of appropriate bases are sodium and potassium hydroxides and hydrides, lithium diisopropylamide (LDA), 1,8-diazabicyclo[5.4.0]undec-7-ene (DBU) and lithium hexamethyldisilane. The reaction temperature may range from about 0° C. to about 100° C. Preferably, the compound of formula VII is reacted with phthalamide in ethanol in the presence of potassium hydroxide at about room temperature.

The above reaction produces a mixture of isomers containing the corresponding compound of the formula VIII, and its C-2 epimer. Crystallization from isopropyl ether yields the compound of formula VIII as the racemate of a single epimer, which is then reduced to produce the corresponding compound of formula IX. Suitable reducing agents include Raney nickel/hydrogen, 10% palladium on charcoal/hydrogen, and aluminum amalgam. Preferably, the reduction is carried out using Raney nickel in ethanol under a hydrogen gas pressure of about 3 atm and at a temperature of about 25° C. Temperatures from about 10° C. to about 60° C. and pressures from about 1 to about 10 atmospheres are also suitable.

Reductive amination of the compound of formula IX from the above step with sodium cyanoborohydride or sodium triacetoxyborohydride and a compound of the formula $R^4CHO$ yields the corresponding compound of formula X. This reaction is typically carried out in a polar solvent such as acetic acid or a lower alkanol, at a temperature from about 0° C. to about 50° C. Acetic acid is the preferred solvent and about 25° C. is the preferred temperature. It is also preferable that the pH of the reaction mixture be about 4 to about 5.

Alternatively, compounds of the formula IX may be converted to the corresponding compounds of the formula X by the two step procedure described above and illustrated in scheme 1 for converting compounds of the formula V into compounds of the formula I-A (V→VI→I-A).

The corresponding compound of formula I-B is then prepared by reacting the compound of formula X from the above step with hydrazine. Usually, this is accomplished using an inert solvent such as a lower ($C_1$-$C_4$) alcohol, water or a mixture of water and a lower alcohol, preferably ethanol, at a temperature from about 20° C. to about the reflux temperature of the solvent, preferably at about the reflux temperature.

The resulting compound of formula I-B may be converted into a compound of the formula I-C by reacting it with a ketone or aldehyde of the formula $R^{10}COR^{11}$, wherein $R^{10}$ is hydrogen or alkyl and $R^{11}$ is alkyl, so that in the resulting compound of formula I-C, $R^1$=$CHR^{10}R^{11}$. This transformation is generally carried out using one of the procedures described above for converting compounds of the formula V into compounds of the formula I-A. Thus, compounds of the formula I-C may be prepared by a two step procedure analogous to the reaction sequence V→VI→I→A described above, in which an imine is formed in the first step, isolated and treated with a reducing agent, or by the equivalent one step procedure in which the imine is formed in situ.

The preparation of compounds of the formula I wherein $R^5$ and one of $R^1$ and $R^2$ is hydrogen, having the depicted relative stereochemistry, ie., the 1-(R,S)-2-(S,R) configuration as defined under the Cahn-Ingold-Prelog system (hereinafter referred to as compounds of the formula I-D) is illustrated in scheme 3.

Referring to Scheme 3, the desired $R^4$ group can be added to the compound of formula XI to form the corresponding compound having formula XII by the one step reductive amination described above for reaction IX→X of scheme 2 or the one step procedure resulting from combining reactions V→VI and VI→I-A in scheme I.

Reaction of the hydrochloride salt of the compound of formula XII so formed with a suitable chlorinating agent yields the corresponding compound of formula XIII. Examples chlorinating agents that may be used are thionyl chloride, phosphorous pentachloride, phosphorus oxychloride and mesyl chloride. This reaction is typically carried out neat or in an inert nonhydroxylic solvent such as methylene chloride, chloroform, 1,2-dichloroethane, benzene or toluene, preferably chloroform, at a temperature from about –2° C. to about 15° C., preferably from about 0° C. to about 5° C.

The corresponding compound of formula I-D can then be prepared as follows. The compound of formula XIII obtained in the preceding step is reacted with a compound of the formula $R^1R^2NH$. This reaction is generally conducted neat or in an inert solvent such as water, THF, tert-butanol, ethanol, dimethylether or acetonitrile, methanol, isopropanol, preferably ethanol, at a temperature from about 0° C. to about the reflux temperature of the solvent, preferably at about the reflux temperature.

The preparation of other compounds of the formula I not specifically described in the foregoing experimental section can be accomplished using combinations of the reactions described above that will be apparent to those skilled in the art.

In each of the reactions discussed or illustrated in schemes 1 to 3 above, pressure is not critical unless otherwise indicated. Pressures from about 0.5 atmospheres to about 5 atmospheres are generally acceptable, and ambient pressure, i.e. about 1 atmosphere, is preferred as a matter of convenience.

The novel compounds of the formula I and the pharmaceutically acceptable salts thereof are useful as substance P antagonists, i.e., they possess the ability to antagonize the effects of substance P at its receptor site in mammals, and therefore they are able to function as therapeutic agents in the treatment of the aforementioned disorders and diseases in an afflicted mammal.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the Formula I from the reaction mixture as a pharmaceutically unacceptable salt and then simply convert the latter back to the free base compound by treatment with, an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The compounds of formula I and their pharmaceutically acceptable salts exhibit substance P receptor-binding activity and therefore are of value in the treatment and prevention of a wide variety of clinical conditions the treatment or prevention of which are effected or facilitated by a decrease in substance P mediated neurotransmission. Such conditions include inflammatory diseases (e.g., arthritis, psoriasis, asthma and inflammatory bowel disease), anxiety, depression or dysthymic disorders, colitis, psychosis, pain, allergies such as eczema and thiniris, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis. Hence, these compounds are readily adapted to therapeutic use as substance P antagonists for the control and/or treatment of any of the aforesaid clinical conditions in mammals, including humans.

The compounds of the formula I and the pharmaceutically acceptable salts thereof can be administered via either the oral, parenteral or topical routes. In general, these compounds are most desirably administered in dosages ranging from about 1.0 mg up to about 1500 mg per day, although variations will necessarily occur depending upon the weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound of the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention as substance P antagonists may be determined by their ability to inhibit the binding of substance P at its receptor sites in bovine eaudate tissue, employing radioactive ligands to visualize the tachykinin receptors by means of autoradiography. The substance P antagonizing activity of the herein described compounds may be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

In this procedure, bovine caudate tissue is removed from a $-70°$ C. freezer and homogenized in 50 volumes (w./v.) of an ice-cold 50 mM Tris (i.e., trimethamine which is 2-amino-2-hydroxymethyl-1,3-propanediol) hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 4 µg/ml of bacitracin, 4 µg/ml of leupeptin, 2 µg of chymostatin and 200 g/ml of bovine serum albumin. This step completes the production of the tissue preparation.

The radioligand binding procedure is then carried out in the following manner, viz., by initiating the reaction via the addition of 100 µl of the test compound made up to a concentration of 1 µM, followed by the addition of 100 µl of radioactive ligand made up to a final concentration 0.5 mM and then finally by the addition of 800 µl of the tissue preparation produced as described above. The final volume is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The anti-psychotic activity of the compounds of the present invention as neuroleptic agents for the control of various psychotic disorders is determined primarily by a study of their ability to suppress substance P-induced or substance P agonist induced hypermotility in guinea pigs. This study is carried out by first dosing the guinea pigs with a control compound or with an appropriate test compound of the present invention, then injecting the guinea pigs with substance P or a substance P agonist by intracerebral administration via canula and thereafter measuring their individual locomotor response to said stimulus.

The present invention is illustrated by the following examples. It will be understood, however, that the invention is not limited to the specific details of these examples.

EXAMPLE 1

1-N-Cyclohexyl-1-phenyl-2-N'-[(2-methoxyphenyl)methyl]1,2-ethanediamine

A. α-Cyclohexylaminobenzeneacetonitrile

A solution of 0.98 g (9.4 mmol) of sodium bisulfite in 4 ml of water was treated with 0.96 ml (9.4 mmol) benzaldehyde in 5 ml of methanol. The resulting mixture was cooled to 5°–10° C. and treated with cyclohexylamine, whereupon a thick precipitate was formed. With the reaction mixture still at approximately 5° C., solid potassium cyanide (0.61 g, 9.4 mmol) was added portionwise over 2 minutes. The precipitate became thick enough to halt stirring and 5 ml of 1:1 methanol water was added to facilitate stirring. The reaction mixture was allowed to warm to room temperature over a 16 hour period. The mixture was then filtered and the product was washed with methanol-water and dried in air. There were obtained 1.6 grams (79.6% yield) of the above titled product. $^1$H NMR (300 MHz, CDCl$_3$) δ7.5-7.3 (m, 5H), 4.82 (s, 1H), 2.9-2.8 (m, 1H), 2.0 (d, 1H, J=12 Hz), 1.75- 1.62 (m, 4H), 1.4-1.0 (m, 6H). $^{13}$C NMR (75 MHz, CDCl$_3$) δ135.56, 128.99, 128.91, 127.29, 119.35, 54.87, 51.68, 33.87, 31.94, 25.95, 24.66, 24.27. IR CHCl$_3$λ 2220 cm$^{-1}$. Mass Spectrum m/e 214 p+.

B. 1-N-Cyclohexyl-1-phenyl-1,2-ethanediamine

A solution of the above described compound from step A (200 mg, 0.94 mmol) in 5 ml of anhydrous toluene was cooled to between 20° C.–10° C. The stirred mixture was treated with 4.67 ml (5 equiv., 4.67 mmol) of diisobutylaluminum hydride (Dibal-H) in toluene solution over a 5 minute period. The reaction mixture was monitored by thin layer analysis (tlc) eluting with 95:4:1 methylene chloride: methanol: conc. aqueous ammonium hydroxide. After 2 hours, the reaction mixture was quenched with 4.6 ml of methanol by dropwise addition to the reaction mixture at 0° C. This was followed by the careful addition of 4.6 ml of water. The reaction mixture was adjusted to pH 2 (with aqueous hydrochloric acid) and was then washed with isopropyl ether. The aqueous layer was separated and made basic to pH 12 with sodium hydroxide, after which the aqueous phase was extracted with methylene chloride. The organic layer was washed with saturated brine and dried with solid sodium sulfate. The crude material was chromatographed on silica gel using the same solvent mixture described above for tlc. There were obtained 150 mg (74%) of the desired material. $^1$H NMR (300 MHz, CDCl$_3$) δ7.37-7.22 (m, 5H), 3.76 (t, 1H, J=8.5 Hz), 2.80 (dd, 1H, J=15.4 Hz, J=8.5 hz), 2.78 (dd, 1H, J=15 hz, J=8.5 Hz), 2.3 (m, 1H), 1.95 (d, 1H, J=10 Hz), 1.69 (br s, 3H), 1.52 (br s, 1H), 1.12 (br s, 6H). $^{13}$C NMR (75 MHz, CDCl$_3$) δ143.20, 128.40, 127.17, 127.03, 62.09, 53.43, 49.20, 34.79, 33.08, 26.16, 24.78. Mass Spectrum m/e 219 p$^{+1}$, 188 p-30.

C. 1-N-Cyclohexyl-1-phenyl-2-N'-[(2 -methoxyphenyl)methyl]-1,2-ethanediamine

The diamine (109 mg 0.5 mmol) from step B was dissolved in 3 ml of acetic acid to which a few 3 Å molecular sieves were added. The mixture was treated with 85 mg (0.625 mmol) anisaldehyde followed by the portionwise addition of 211 mg (1.0 mmol) of sodium triacetoxyborohydride. The reaction mixture was stirred for two hours. The reaction mixture was filtered and evaporated in vacuo. The residue was taken up in 10 ml of 1 N hydrochloric acid (HCl) and extracted with ether. The aqueous phase was separated and the solution pH was adjusted to 12 with 2 M sodium hydroxide (NaOH). The aqueous phase was extracted with ether which was then washed with brine, dried with sodium sulfate and evaporated in vacuo. The residue was chromatographed on silica gel using 97:2:1 methylene chloride: methanol: conc. aqueous ammonium hydroxide as the eluant. There were obtained 70 mg (41%). $^1$H NMR (300 MHz, CDCl$_3$) δ7.33-7.18 (m, 7H), 6.88 (t, 1H, J=7.4 Hz) , 6.82 (d, 1H, J=8.0 Hz) , 3.94 (dd, 1H, J=8.06 Hz, J=5.50 Hz), 3.78 (s, 2H), 3.73 (s, 3H), 2.76-2.64 (m, 2H), 2.31-2.25 (m, 1H), 2.00-1.53 (m, 7H), 1.10 (br s, 5H). $^{13}$C NMR (75 MHz, CDCl$_3$) δ157.61, 143.69, 129.82, 128.33, 128.13, 127.21, 126.92, 120.34, 110.14, 59.09, 56.24, 55.11, 53.56, 49.09, 34.94, 32.99, 26.24, 25.23, 24.87 ppm. IR CHCl$_3$ λ 1600(d), 1450 cm$^{-1}$. Mass spectrum m/e 339 p$^{30\ 1}$.

The dihydrochloride salt of the title compound was prepared by dissolving 70 mg (0.2 mmol) in ether and treating the solution with an excess of hydrogen chloride (HCl) saturated ether. The salt was obtained after evaporation of the solvent and dissolution of the residue in small amount of methanol and precipitation with isopropyl ether. M.p. 222°–224° C. Anal. Calc'd for C$_{22}$H$_{30}$N$_2$O.2HCl: C, 64.23; H, 7.84; N, 6.81%. Found: C, 63.97; H, 7.86; N, 6.73%.

EXAMPLE 2

1-N-Cyclopentyl-1-phenyl-2-N'-(2-methoxyphenyl)methyl]-1,2-ethanediamine

This compound was prepared by a procedure similar to that described in Example 1. $^1$H NMR (300 MHz, CDCl$_3$) δ7.34-7.17 (m, 7H) , 6.88 (t, 1H, J=7.37 Hz) , 6.82 (d, 1H, J=8.14 Hz), 3.80 (dd, 1H, J=8.11 Hz, J=5.57 Hz), 3.78 (s, 2H), 3.74, (s, 3H), 2.88 (quin, 1H, J=6.80 Hz), 2.77-2.66 (m, 2H), 1.95 (br s, 1H), 1.80-1.20 (m, 8H). $^{13}$C NMR (75 MHz, CDCl$_3$) δ157.5, 143.16, 129.86, 128.34, 128.20, 127.35, 127.05, 120.35, 110.14, 61.07, 57.14, 55.88, 55.11, 49.12, 34.03, 32.60, 23.82, 23.78. IR CHCl$_3$ λ 1605 (d), 1450 cm$^{-1}$. Mass spectrum m/e 325 p$^{+1}$. High Resolution Mass Spectrum (HRMS) calc'd for C$_{21}$H$_{29}$N$_2$O (p+1): 325.2273. Found: 325.2250.

The dihydrochloride salt of the title compound was prepared as described in Example 1C. M.p.=223°–224° C. Anal Calc'd for C$_{21}$H$_{28}$N$_2$O.2HCl: C, 63.47; H, 7.61; N, 7.05%. Found: C, 63.46; H, 7.61; N, 7.02%.

EXAMPLE 3

1-N-propyl-1-phenyl-2-N'-[(2-methoxyphenyl)methyl]-1,2-ethanediamine

The title compound as prepared by a procedure similar to that described in Example 1. $^1$H NMR (300 MHz, CDCl$_3$) δ 7.34-7.18 (m, 7H), 6.89 (dr, 1H, 7.39 Hz, J=1.04 Hz), 6.83 (d, 1H, J=8.10 Hz), 3.79 (m, 2H), 3.75 (s, 3H), 3.74-3.70 (m, 1H), 2.80-2.67 (m, 2H), 2.43-2.38 (m, 2H), 1.52-1.40 (m, 2H), 0.893-0.844 (t, 3H, J=7.37 Hz). $^{13}$C NMR (75 MHz, CDCl$_3$) δ 157.62, 143.07, 129.82, 128.36, 128.17, 127.30, 127.05, 120.35, 110.17, 62.88, 55.88, 55.13, 49.69, 49.21, 29.72, 23.42, 11.85 ppm. IR CHCl$_3$ λ 1600(d), 1450 cm$^{-1}$. Mass spectrum m/e 229 p$^{+1}$.

EXAMPLE 4

1-(R,S)-2-(R,S)-1-Amino-1-phenyl-2-[(2-methoxy)-phenylmethylamino]propane

A. 1-(R,S)-2-(R,S)-1-N-Phthalimido-1-phenyl-2nitropropane

A solution of phthalimide (20.0 g, 135.93 mmol) in 400 ml of ethanol was treated with 9.87 g (149.53 mmol) of potassium hydroxide and stirred for 15 minutes. The mixture was treated with 28.80 g (176.71 mmol) of 1-phenyl-2-nitropropene and the reaction mixture was stirred at room temperature for 18 hours. The reaction mixture was quenched with 72.71 g (1.35 mol) of solid ammonium chloride and then diluted with 100 ml of ethyl acetate and 1500 ml of water. The aqueous layer was extracted (6×300 ml) with ethyl acetate. The combined organic layers were dried with magnesium sulfate and evaporated. The residue (yellow paste) was treated with 250 ml of isopropyl ether and stirred for 5 minutes. The solids were filtered and washed with 50 ml isopropyl ether and then 3×60 ml of ethanol followed by air drying. There were obtained 18.35 g of a mixture containing the desired material as a single isomer contaminated only by phthalimide. The crude material was used directly in the next step.

B. 1-(R,S)-2-(R,S)-1-N-Phthalimido-1-phenyl-2-aminopropane

A mixture of 125 g Raney nickel (prewashed with water until the aqueous supernatent was neutral (pH 7)) was charged into a 500 ml Parr bottle which was flushed with nitrogen. To the system were added 20 ml of methanol followed by 9.0 g of the crude product from the previous step and the mixture was diluted with 200 ml of methanol. The mixture was placed under a hydrogen atmosphere at 45 psi for 12 hours. Thin layer analysis (tlc) (5% methanol in methylene chloride) indicated that starting material had been consumed. The catalyst was removed by filtration through Celite® and the filtrate was evaporated in vacuo. The residue was treated with 100 ml of methylene chloride whereupon residual phthalimide precipitated. The mixture was filtered once again and the filtrate was evaporated in vacuo. The residue was chromatographed on silica gel eluting with 2% methanol in methylene chloride. There were obtained 2.65 g (%) of the title compound as a single isomer. $^1$H NMR (250 MHz, CDCl$_3$) δ 7.83-7.80 (2H, m), 7.72-7.67 (2H, m), 7.60-7.56 (2H, m), 7.37-7.28 (3H, m), 4.90- 4.86 (1H, d, J=10.6 Hz), 4.41-4.29 (1H, dq, J=10.6 Hz, J=6.4 Hz), 1.44 (2H, br s), 1.10-1.06 (3H, d, J=6.4 Hz).

C. 1-(R,S)-2-(R,S)-1-N-Phthalimido-1 -phenyl-2-[(2-methoxy)phenyl-methylamino]propane A solution of 2.18 g (7.77 mmol) of the product from step B in 75 ml of toluene was treated with 1.06 g (7.77 mmol) of 2-methoxybenzaldehyde. The resulting reaction mixture was heated to reflux over a Dean-Stark water separator for 16 hours. The reaction was then cooled to room temperature and was evaporated in vacuo to afford 3.10 g of an imine as a yellow solid which was used without purification. $^1$H NMR (250 MHz, CDCl$_3$) δ 8.77 (s, 1H), 7.73- 7.69 (m, 5H), 7.59-7.54 (m, 2H), 7.39-7.23 (m, 5H), 6.84-6.77 (m, 2H), 5.50 (d, 1H, J=10.7 hz), 4.93-4.83 (dq, 1H, J=10.7 Hz, J=6.4 Hz), 3.76 (s, 3H), 1.20-1.17 (d, 3H, J=6.4 Hz). A solution of the above described imine (3.07 g, 7.70 mmol) was taken up in 70 ml of dichloroethane was treated with 1.64 g (7.70 mmol) of sodium triacetoxyborohydride. The reaction mixture was stirred for 1.5 hours and was monitored by thin layer analysis ( 1% methanol in methylenechloride). At this point, 1.64 g of sodium triacetoxyborohydride were added and stirring was continued for an additional 16 hours. The reaction mixture was quenched with 300 ml of saturated aqueous bicarbonate and the mixture was extracted with 2 volumes of dichloroethane. The combined organic layers were washed with aqueous brine solution and dried with magnesium sulfate. The residue was chromatographed on silica gel using 20% ethyl acetate in hexane as eluent to provide 2.59 g (84%) of an oil. $^1$H NMR (250 MHz, CDCl$_3$) δ 7.81-7.78 (m, 2H), 7.71-7.66 (m, 2H), 7.61-7.58 (m, 2H), 7.35-7.25 (m, 4H), 7.21-7.13 (m, 2H), 6.84-6.78 (dt, 1H, J=7.37 Hz, J=1.0 Hz), 6.74-6.71 (d, 1H, J=8.17 Hz), 5.30 (s, 1H), 5.09-5.05 (d, 1H, 10.96 Hz), 4.22-4.15 (dq, 1H, J=10.96 Hz, J=6.36 Hz), 3.90-3.68 (dd, 2H, J=13.0 Hz), 3.54 (s, 3H), 1.05-1.03 (d, 3H, J=6.36 Hz).

D. 1-(R,S)-2-(R,S)-1-Amino-1-phenyl-2-[(2-methoxy)phenylmethylamino]propane

A solution of 2.38 g (5.94 mmol) of 1-N-phthalimido-1 -phenyl-2-[(2-methoxy)phenylmethylamino]propane, prepared by the procedure of step C, in 85 ml of ethanol was treated with 281 µl (5.94 mmol) hydrazinc hydrate and the reaction mixture was heated to reflux. After 2.5 hours, the mixture was allowed to cool to room temperature and was stirred overnight. The reaction mixture was treated with 1.48 ml (17.83 mmol ) of concentrated hydrochloric acid. The resulting suspension was filtered and the filtrate was diluted with water (200 ml) and was washed with ether (5×100 ml). The aqueous layer was adjusted to pH 12 with 25% NaOH solution and the basic phase was extracted with ethyl acetate (3×100 ml). The organic layer was dried over sodium sulfate and stripped to an oil. There was obtained 1.18 g (73% yield). $^1$H NMR (250 MHz, CDCl$_3$) δ 7.36-7.22 (m, 7H), 6.95-6.83 (m, 2H), 3.95 & 3.72 (dd, 2H, J=13.3 Hz), 3.77 (s, 3H) , 3.73 [d(obsc), 1H], 2.79-2.73 (dq, 1H, J=6.38 Hz, J=7.55 Hz), 2.01 (br s, 3H), 0.99-0.96 (d, 3H, J=6.38 Hz). $^{13}$C NMR (75.47 MHz, CDCl$_3$) δ 157.64, 144.67, 129.88, 128.39, 128.32, 127.97, 127.02, 120.46, 110.20, 61.33, 58.26, 55.19, 46.80, 17.15 ppm. IR (CHCl$_3$) λ 1601, 1487, 1461 cm$^{-1}$. High Resolution Mass Spectrum (HRMS) calc'd for C$_{17}$H$_{22}$N$_2$O (p+1): 271.18103. Found: 271.1802.

The dihydrochloride was prepared by treating a solution of the above prepared diamine in ether with a saturated solution of hydrogen chloride in ether. The mixture was evaporated and the residue was taken up in methanol, filtered through glass wool and recrystallized from methanol/ether. M.p. 244°-245° C. Anal. calc'd for C, 59.48; H, 7.05; N, 8.16. Found: C, 59.31; H, 7.01; N, 8.00.

EXAMPLE 5

1R·,
2S·)-1-Cyclohexylamino-1-phenyl-2-[(2-methoxy)- phenylmethylamino]propane

A. (1R, 2S)-1-Hydroxy-1-phenyl-2-[(2-methoxy)-phenyl-methylamino]propane

A solution of 1.00 g (6.61 mmol) (1R, 2S)-(-)-norephedrine and 1.12 g (8.26 mmol) of o-anisaldehyde in 20 ml of acetic acid was treated with 1.5 g of 3 Å molecular sieves. The mixture was treated with 2.8 g (13.22 mmol) of sodium triacetoxyborohydride in 0.1 g increments over 20 minutes. The reaction mixture was stirred at room temperature for 18 hours under a nitrogen atmosphere. The reaction was judged to be complete by thin layer analysis (eluting with 9:1 methylene chloride:methanol), the mixture was filtered and the filtrate was evaporated in vacuo. The residue was taken up in 25 ml of water and the mixture was treated with 1N HCl until the solution pM was approximately 3. The aqueous phase was extracted twice with ether (25 ml) and was then treated with 2N NaOH until pH 12 was reached. The aqueous layer was again extracted with ether (3×50 ml). The organic layer was dried with magnesium sulfate and was evaporated to dryness. There were obtained 1.11 g (62% yield) of a white solid after chromatography (eluting with 95% ethyl acetate/5% triethyl amine) on silica gel. M.P. 84°-86° C. $^1$H NMR (CDCl$_3$, 300 MHz) δ 7.39-7.21 (7 H, m), 7.0-6.92 (1H, t, J=8.5 Hz), 6.91-6.88 (1H, d, J=8.0 Hz), 4.82 (d, 1H, J=4.0 Hz), 3.90 (s, 2H), 3.82 (s, 3H), 2.97-2.88 (dq, 1H, J=7 Hz, J=4.0 Hz), 0.82 (d, 3H, J=7 Hz) ppm. $^{13}$C NMR (DEPT, CDCl$_3$, 75.47 MHz) δ 157.74 (s), 141.65 (s), 129.86 (d) , 128.50 (d), 128.14 (s), 128.05 (d), 126.93 (d), 126.12 (d), 120.49 (d), 110.36 (d), 72.83 (d), 57.25 (d), 55.23 (q), 46.68 (t), 14.77 (q) ppm. IR (KBr) λ 3500-2400 (br), 1600, 1480, 1460, 1240, 1050, 1030 cm$^{-1}$. HRMS calc'd for C$_{17}$H$_{21}$NO$_2$: 271.1567. Found 271.1603.

B. (1R,S,2S)-1-Chloro-1-phenyl-2-[2-methoxyphenyl)methylamino]propane

A solution of the hydrochloride salt of the title compound of Example 5A was prepared by addition of 2.1 g (6.82 mmol) of (1R, 2S)-1-hydroxy-1-phenyl-2-[(2-methoxy)phenylmethylamino]propane to a saturated solution of hydrogen chloride (HCl) gas in methylene chloride followed by evaporation in vacuo. The residue was dissolved in 0.75 ml (10.23 mmol) of thionyl chloride and the mixture was heated to reflux. After a period of 40 minutes, the reaction mixture was evaporated in vacuo to yield the product as a mixture of two diastereomers (2.8:1 ratio by $^1$H NMR) and as a yellow solid which was used directly in part D.

C. (1R,S,2S)-1-Chloro-1-phenyl-2-[(2-methoxyphenyl)methylamino]propane

A solution of the hydrochloride salt of the title compound of example 5A was prepared by addition of 1.0 g (3.69 mmol) of (1R, 2S)-1-hydroxy-1-phenyl-2-[(2-methoxy)phenylmethylamino]-propane to a saturated solution of HCl (g) in methylene chloride followed by evaporation in vacuo. The residue was dissolved in 10 ml of chloroform and chilled to 5° C. To the solution 0.66 gm (5.53 mmol) of thionyl chloride in 10 ml of chloroform was added slowly via syringe and the mixture was allowed to warm to room temperature. After a period of 40 minutes the reaction mixture was evaporated in vacuo to yield the product as a mixture of two diastereomers (44%:55% ratio by $^1$H NMR) and as a yellow solid which was used directly in part D.

D. (1R·,2S·)-1-Cyclohexylamino-1-phenyl-2-[(2-methoxy)phenylmethylamino]propane

A solution of the previously prepared (1R, S, 2S)-1-chloro-1-phenyl-2-[(2-methoxy)phenyl-methylamino]propane in ethanol [1.0 g (3.06 mmol) in 5 ml] was treated with 1.05 ml (9.19 mmol) cyclohexylamine and the reaction mixture was heated to reflux for 50 minutes. The reaction mixture was allowed to cool to room temperature and was then filtered to remove a small amount of a white precipitate. The filtrate was evaporated in vacuo and the residue was chromatographed on silica gel eluting with hexane:ethyl acetate (7:3). The minor, more polar material was collected (80 mg) and was dissolved in ether and treated with a saturated solution of HCl (g) in ether. The resulting gummy solid was collected and repulped in petroleum ether to afford 90 mg of the dihydrochloride salt as a light tan solid. M.p. 173°–181° C. (decorap.). $^1$H NMR free base (CDCl$_3$, 300 MHz) δ7.32-7.14 (m, 7H), 6.88 (t, 1H, J=7 Hz), 6.78 (d, 1H, J=7 Hz), 3.78 (dd, 2H, J=13 Hz), 3.82 [d(obsq), 1H], 3.7 (s, 3H), 2.76 (quin, 1H, J=6 Hz), 2.24-2.12 (m, 1H), 2.0-1.46 (m, 7 H), 1.19-1.0 (m, 4H), 0.98 (d, 3H, J=6 Hz) ppm. $^{13}$C NMR (CDCl$_3$, 75.47 MHz) δ 157.67, 142.84, 129.85, 128.53, 128.15, 128.08, 128.02, 126.63, 120.30, 110.09, 62.58, 56.97, 55.05, 53.63, 46.82, 34.97, 32.96, 26.30, 25.29, 24.91, 16.2, 14.24 ppm. IR (CHCl$_3$) λ 1600, 1450 cm$^{-1}$. HRMS C$_{23}$H$_{32}$N$_2$O (no p+ found). Calc'd for C$_{10}$H$_{14}$NO: 164.075. Found: 164.1066. Calc'd for C$_{13}$H$_{18}$N: 188.1439. Found: 188.1441.

The title compounds of Examples 6–9 were prepared by a method analogous to that described in Example 1.

EXAMPLE 6

1-N-cyclohexyl-1-phenyl-2-N'-[(2-methoxy-5-trifluoromethoxyphenyl)methyl]-1,2-ethanediamine HRMS m/e Calc'd for C$_{23}$H$_{29}$N$_2$O$_2$F$_3$: 422. 2174. Found 422.21356.

EXAMPLE 7

1-N-pyrrolidyl-1-phenyl-2-N'-[(2-methoxyphenyl)methyl]-1,2-ethanediamine dihydrochloride Calc'd for C$_{20}$H$_{26}$N$_2$O.2HCl: C: 62.66, H: 7.36, N: 7.31. Found C: 62.26, H: 7.38, N: 7.33.

EXAMPLE 8

1-N-methyl-1-phenyl-2-N'-[(2-methoxyphenyl)methyl]-1,2-ethanediamine dihydrochloride Calc'd for C$_{17}$H$_{22}$N$_2$O.2HCl: C: 59.48, H: 7.05, N: 8.16. Found C: 59.39, H: 7.25, N: 8.02.

EXAMPLE 9

1-N-phenylmethyl-1-phenyl-2-N'-[(2-methoxyphenyl)methyl]-1,2-ethanediamine dihydrochloride Calc'd for C$_{23}$H$_{26}$N$_2$O.2HCl: C: 65.87, H: 6.73, N: 6.68. Found C: 65:63, H: 6.77, N: 6.64.

EXAMPLE 10

1-N-cyclooctyl-1-phenyl-2-N'-[(2-methoxyphenyl)methyl]1,2-ethanediamine dihydrochloride Calc'd for C$_{24}$H$_{34}$N$_2$O.2HCl: C: 65.59, H: 8.26, N: 6.37. Found C: 65.60, H: 8.19, N: 6.20.

EXAMPLE 11

1-N-phenyl-1-phenyl-2-N'-[(2-methoxyphenyl)methyl]-1,2-ethanediamine dihydrochloride Calc'd for C$_{22}$H$_{24}$N$_2$O.1HCl: C: 71.63, H: 6.83, N: 7.59. Found C: 71.26, H: 6.83, N: 7.65.

EXAMPLE 12

1-N-phenyl-1-phenyl-2-N'-[(2-methoxyphenyl)methyl]-1,2-ethanediame dihydrochloride Calc'd for C$_{20}$H$_{26}$N$_2$O.2HCl: C: 62.66, H: 7.36, N: 7.31. Found C: 62:26, H: 7.48, H: 7.24.

EXAMPLE 13

1-N-2-adamantyl)-1-phenyl-2-N'-[(2-methoxyphenyl)methyl]1,2-ethanediamine dihydrochloride Calc'd for C$_{26}$H$_{34}$N$_2$O.2HCl: C: 67.38, H: 7.83, N: 6.04. Found C: 67.23, H: 8.04, N: 6.10.

EXAMPLE 14

1-N-(1-dimethylethyl)-1-phenyl-2-N'-[(2-methoxyphenyl)methyl]-1,2-ethanediamine dihydrochloride 2-HCl Salt mp=155°–157° C.

EXAMPLE 15

1-N-cyclopropyl-1-phenyl-2-N'-[(2-methoxyphenyl)methyl]-1,2-ethanediamine dihydrochloride 2-HCl Salt mp=140°–141° C.

EXAMPLE 16

1-N-isopropyl-1-phenyl-2-N'-[(2-methoxyphenyl)methyl]-1,2-ethanediamine dihydrochloride Calc'd for $C_{19}H_{26}N_2O.2HCl$: C: 61.45, H: 7.60, N: 7.54. Found C: 61.19, H: 7.67, N: 7.52.

EXAMPLE 17

1-N-(1-phenylethyl)-1-phenyl-2-N'-[(2-methoxyphenyl)methyl]-1,2-ethanediamine dihydrochloride 2-HCl Salt mp=226°–228° C.

EXAMPLE 18

1-N-(2-norbornyl)-1-phenyl-2-N'-[(2-methoxyphenyl)methyl]-1,2-ethanediamine dihydrochloride Calc'd for $C_{23}H_{30}N_2O.2HCl$: C: 65.24, H: 7.62, N: 6.62. Found C: 65.48, H: 7.95, N: 6.65.

EXAMPLE 19

1-N-2-aza-bicyclo[4.4.0]decane)-1-phenyl-2-N'-[(2-methoxyphenyl)methyl]-1,2-ethanediamine dihydrochloride HRMS m/e Calc'd for $C_{25}H_{34}N_2O$: 378.2663. Found 378.270 2.

EXAMPLE 20

1,1-Diphenyl-2-N'-[(2-methoxyphenyl)methyl]-1,2-ethanediamine

A. α,α-Diphenyl-α-aminoacetonitrile

A solution of 4.05 ml (0.03 mol) of trimethylsilylcyanide in 20 ml of dry benzene was treated with 0.44 gm (0.001 mol) zinc iodide and 4.63 ml (0.028 mol) of benzophenoneimine. The reaction mixture was stirred at room temperature for 10 min., whereupon a white precipitate formed. The reaction mixture was quenched with wet ether and stirred for 2 hours. The liquid phase was washed with saturated brine solution and dried over sodium sulfate and evaporated in vacuo. The residue was recrystallized from ether-hexane to afford 2.4 gm (38%). $^1$H NMR (CDCl$_3$, 300 MHz) δ 7.7-7.6 (m, 4H), 7.4-7.28 (m, 6H); $^{13}$C NMR (CDCl$_3$, 75.5 MHz) δ 141.2, 128.9, 128.6, 125.8, 123.4, 60.8.

B. 1,1-Diphenyl-1,2-ethanediamine

α,α-Diphenyl-α-aminoacetonitrile (1.0 gm, 0.0048 mol) was dissolved in 6 ml of toluene and was cooled to −20° C. The solution was treated with 19.2 ml (0.0192 mol) of 1 M diisobutylaluminum hydride (DiBal-H) and stirred at −20° C. for 3 hours. The reaction mixture was quenched with 2.0 ml of methanol followed by 50 ml of water. The reaction mixture was acidified to pH 1.0 and the aqueous phase was extracted with ether several times. The remaining aqueous phase was basified to pH 13 with 2N sodium hydroxide solution and extracted with methylene chloride. The organic phase was dried and evaporated to afford 0.946 g (92%) of the desired material as an oil.

$^1$H NMR (CDCl$_3$, 300 MHz) δ 7.38-7.15 (m, 10H), 3.35 (s, 2H); $^{13}$C NMR (CDCl$_3$, 75.5 MHz) δ 147.0, 128.3, 126.8, 126.6, 62.1, 52.4.

C. 1,1-Diphenyl-2-N'-[(2-methoxyphenyl)methyl]-1,2-ethanediamine 1,1-Diphenyl-1,2-ethanediamine (25 mg, 0.118 mmol) prepared in the previous step was dissolved in 2 ml of acetic acid and treated with 44 mg 3 A molecular sieves. The stirred mixture was treated with 20 mg (0.147 mmol) oanisaldehyde followed by portionwise addition of 25 mg (0.118 mmol) sodium triacetoxyborohydride. The reaction mixture was stirred for 2 hours and was then diluted with 20 ml of water, acidified to pH 1 with aqueous 2N HCl aq and extracted with ether. The aqueous phase was basified with aqueous sodium bicarbonate and extracted with methylene chloride. The organic phase was washed with brine and then dried and evaporated. The residue was chromatographed on silica eluting with 96:3:1 CH$_2$Cl$_2$:MeOH:NH$_4$OH. There was obtained 39 mg (68%) of the title material. $^1$H NMR (CDCl$_3$, 300 MHz) δ7.38-7.12 (m, 12H), 6.90 (t, 1H, J=7 Hz), 6.8 (d, 1H, J=8 Hz), 3.8 (s, 2H); 3.65 (s, 3H), 3.25 (s, 2H); $^{13}$C NMR (CDCl$_3$, 75.5 MHz) δ 157.6, 147.2, 129.7, 128.3, 128.1, 126.7, 126.5, 120.3, 110.1, 61.1, 59.6, 55.0, 49.9;

HRMS calc'd for $C_{22}N_{24}N_2O$ 332.1883; found 332.18684.

The title compounds of Examples 20A–22 were prepared by a procedure analogous to that described in Example 20.

EXAMPLE 20

1,1-diphenyl-2-N'-[(2-methoxyphenyl)methyl]-1,2-ethanediamine dihydrochloride

Calc'd for $C_{22}H_{24}N_2O.2HCl.0.5\ H_2O$: C: 63.77, H: 6.57, N: 6.76. Found C: 64.03, H: 6.72, N: 6.78

EXAMPLE 21

1,1-diphenyl-2-N'-[(2,5-dimethoxyphenyl)methyl]-1,2-ethanediamine

HRMS m/e Calc'd for $C_{25}H_{34}N_2O$: 363.2066. Found 363.20730.

EXAMPLE 22

1,1-diphenyl-2-N'-[(2,4-dimethoxyphenyl)methyl]-1,2-ethanediamine dihydrochloride Calc'd for $C_{23}H_{26}N_2O_2.2HCl$: C: 63.45, H: 6.48, N: 6.43 Found C: 63.07, H: 6.36, N: 6.31.

The title compounds of Examples 23–28 were prepared by a method analogous to that described in Example 1.

EXAMPLE 23

1-N-cyclohexyl-1-N-(6-n-hexanol)-1-phenyl-2-N'-[(2-methoxyphenyl)methyl]-1,2-ethanediamine ms m/e 439 (p+1)

EXAMPLE 24

1-N-cyclohexyl-1-N-(3-phenylpropyl)-1-phenyl-2-N'-[(2-methoxyphenyl)methyl]-1,2-ethanediamine ms m/e 457 (p+1)

EXAMPLE 25

3,3-diphenyl-2-N-cyclopentyl-1-N'-[(2-methoxyphenyl)methyl-1,2-propanediamine dihydrochlorid Calc'd for $C_{28}H_{34}N_2O.2HCl$: C: 68.98, H: 7.44, N: Found C: 68.69, H: 7.79, N: 5.47.

EXAMPLE 26

1-N-(2-phenylethyl)-1-(3,4-methylenedioxyphenyl)-2-N'methoxyphenyl)methyl]-1,2,-ethanediamine dihydrochlorid Calc'd for $C_{25}H_{28}N_2O_3.2HCl$: C: 62.89, H: 6.33, N: Found C: 62.90, H: 6.09, N: 5.82.

EXAMPLE 27

1-N-cyclopentyl-1-(2-napthyl)-2-N'-[(2-methoxyphenyl)methyl]-1,2-ethanediamine dihydrochlorid Calc'd for $C_{25}H_{30}N_2O.2HCl$: C: 67.11, H: 7.21, N: Found C: 66.75, H: 7.12, N: 6.07.

EXAMPLE 28

1-N-cyclohexyl-1-cyclohexyl-2-N'-[(2-methoxyphenyl)methyl]-1,2-ethanediamine dihydrochlorid Calc'd for $C_{22}H_{36}N_2O.2HCl$: C: 63.30, H: 9.18, N: Found C: 63.31, H: 9.58, N: 6.72.

The title compounds of Examples 29–34 were prepar a procedure analogous to that described in Example 4:

EXAMPLE 29

(1R,S)-cycloheptylamino-1-phenyl-(2R,S)-[(2-methoxyphenyl)methylamino]propane

HRMS m/e Calc'd for $C_{24}H_{35}N_2O$ (FAB, p+1) 367.27492. 367.2752.

EXAMPLE 30

(1R,S)-amino-1-phenyl-(2R,S)-[(2-methoxyphenyl)methylamino]propane

HRMS m/e Calc'd for $C_{17}H_{23}N_2O$ (FAB, p+1) 271.18103. 271.1802.

EXAMPLE 31

(1R,S)-(4-pyranyl)amino-1-phenyl-(2R,S)-[(2-methoxyphenyl)methylamino]propane

HRMS m/e Calc'd for $C_{22}H_{31}N_2O_2$ (FAB, p+1) 355.2 Found 355.2391.

EXAMPLE 32

(1R,S)-cyclohexylamino-1-phenyl-(2R,S)-[(2-methoxyphenyl)methylamino]propane

Ms m/e (FAB) 353 (p+1).

EXAMPLE 33

(1R,S) -cyclopentylamino-1-phenyl-(2R,S)-[(2-methoxyphenl)methylamino]propane dihydrochloride Calc'd for $C_{22}H_{30}N_2O.2HCl$: C: 64.23, H: 7.84, N: 6.81. Found C: 63.83, H: 7.76, N: 6.71.

EXAMPLE 34

(1R,S)-n-propylamino-1-phenyl-(2R,S)-[(2methoxyphenyl)methylamino]propane

Ms m/e (FAB) 313 (p+1).

The title compounds of Examples 35–42 were prepared by a method analogous to that described in Example 5.

EXAMPLE 35

(1R,S)-cyclohexylamino-1-phenyl-(2S,R)-[(2-methoxyphenyl)methylamino]propane dihydrochloride Calc'd for $C_{23}H_{32}N_2O.2HCl0.5 H_2O$: C: 63.59, H: 8.12, N: 6.45. Found C: 63.29, H: 8.27, N: 6.24.

EXAMPLE 36

(1R,S)-N-pyrrolidyl-1-phenyl-(2S,R)-[(2-methoxyphenyl)methylamino]propane dihydrochloride Calc'd for $C_{21}H_{28}N_2O.2HCl0.5 H_2O$: C: 62.07, H: 7.69, N: 6.89. Found C: 62.11, H: 7.82, N: 6.96.

EXAMPLE 37

(1R,S)-piperidyl-1-phenyl-(2S,R)-[(2-methoxyphenyl)methylamino]propane

HRMS m/e Calc'd for $C_{22}H_{31}N_2O$ (p+1): 339.2429. Found 339.2393.

EXAMPLE 38

(1R,S)-cyclopentylamino-1-phenyl-(2S,R)-[(2-methoxyphenyl)methylamino]propane

HRMS m/e Calc'd for $C_{22}H_{31}N_2O$ (p+1): 339.2429. Found 339.2421.

EXAMPLE 39

(1R,S)-cyclooctylamino-1-phenyl-(2S,R)-[(2-methoxyphenyl)methylamino]propane dihydrochloride Calc'd for $C_{25}H_{36}N_2O.2HCl$: C: 66.21, H: 8.45, N: 6.18. Found C: 65.88, H: 8.78, N: 5.98.

EXAMPLE 40

(1R,S)-propylamino-1-phenyl-(2S,R)-[(2-methoxyphenyl)methylamino]propane

HRMS m/e Calc'd for $C_{20}H_{28}N_2O$: 312.2195. Found 312.2169.

EXAMPLE 41

(1R,S)-methylamino-1-phenyl-(2S,R)-[(2-methoxyphenyl)methylamino]-3-methoxypropane HRMS m/e Calc'd for $C_{19}H_{26}N_2O_2$: 314.1918. Found 314.1718.

EXAMPLE 42

(1R, S)-amino-1-phenyl-(2S,R)-[(2-methoxyphenyl)methylamino]-3-methoxypropane

Ms m/e (FAB) 301 (p+1).

The title compounds of Examples 43 to 46 were prepared by a method analogous to that described in Example 1.

EXAMPLE 43

1-N-cyclohexyl-1-phenyl-2-N'-[(2-methoxy-5-tertbutylphenyl)methyl]-1,2-ethanediamine $^1$H NMR (CDCl$_3$, 250 MHz) δ 7.35-7.22 (m, 7H), 6.78 (br.d, 1H, J=10.7 Hz), 3.99 (dd, 1H, J=7.9 Hz, J=6.4 Hz), 3.79 (s, 2H), 3.72 (s, 3H), 2.75 (m, 2H), 2.31 (m, 1H), 2.02-1.51 (m, 7H), 1.30 (s, 9H), 1.25-1.0 (m, 3H) ppm.

$^{13}$C NMR (CDCl$_3$, 75.47 MHz) δ 155.42, 143.55, 142.98, 128.34, 127.20, 127.00, 126.94, 124.62, 109.67, 58.93, 56.15, 55.17, 53.54, 49.38, 34.91, 34.04, 32.94, 31.55, 26.21, 25.17, 24.82 ppm.

IR (neat) λ3300 (w), 2940, 1610 (w), 1510, 1460, 1375, 1250 cm$^{-1}$.

Mass spectrum m/e 394 (p+).

EXAMPLE 44

1-N-cyclohexyl-1-phenyl-2-N'-[(2-methoxy-5-isopropylphenyl)methyl]-1,2-ethanediamine $^1$H NMR (CDCl$_3$, 300 MHz) δ 7.35-7.20 (m, 6H), 7.06 (br.s, 1H), 6.77 (d, 1H, J=8.6 Hz), 3.96 (dd, 1H, J=8.0 Hz, J=5.6 Hz), 3.75 (s, 2H), 3.71 (s, 3H), 2.90-2.65 (m, 3H), 2.30 (m, 1H), 2.02-1.49 (m, 7H), 1.22 (d, 6H, J=6.9 Hz), 1.25-0.95 (m, 5H) ppm.

$^{13}$C NMR (CDCl$_3$, 75.47 MHz) δ 155.74, 143.64, 140.70, 128.33, 128.02, 127.21, 126.93, 125.58, 110.03, 58.99, 56.24, 55.21, 53.55, 49.24, 34.92, 33.28, 32.96, 26.22, 25.19, 24.83, 24.24, 24.22 ppm.

IR (neat) λ 3300 (w), 2930, 1610 (w), 1510, 1455, 1250 cm$^{-1}$.

Mass spectrum m/e 380 (p+).

EXAMPLE 45

1-N-cyclohexyl-1-phenyl-2-N'-[(2-methoxy-4,5-dimethyl-phenyl)methyl]-1,2-ethanediamine $^1$H NMR (CDCl$_3$, 300 MHz) δ 7.34-7.20 (m, 5H), 6.93 (s, 1H), 6.62 (s, 1H), 3.94 (dd, 1H, J=8.1 Hz, J=5.4 Hz), 3.71 (s, 3H), 3.71 (s.obsc, 2H), 2.73 (dd, 1H, J=11.7 Hz, J=5.4 Hz), 2.66 (dd, 1H, J=11.7 Hz, J=8.1 Hz), 2.30 (m, 1H), 2.23 (s, 3H), 2.17 (s, 3H), 2.0-1.5 (m, 7H), 1.07 (m, 5H) ppm.

$^{13}$C NMR (CDCl$_3$, 75.47 MHz) δ 155.65, 143.79, 135.99, 131.31, 128.30, 127.85, 127.25, 126.87, 125.51, 112.02, 59.10, 56.27, 55.29, 53.57, 48.77, 34.95, 32.97, 26.25, 25.23, 24.88, 19.93, 18.70 ppm.

IR (neat) λ 3300 (w), 2910, 2840, 1610 (w), 1500, 1450 (sh), 1250, 1200 cm$^{-1}$.

Mass spectrum m/e 367 (p+$^1$).

EXAMPLE 46

1-N-cyclohexyl-1-N-(6-hydroxyhexyl)-1-phenyl-2-N'-[(2-methoxyphenyl)methyl]-1,2-ethanediamine $^1$H NMR (CDCl$_3$, 250 MHz) δ 7.30-7.17 (m, 7H), 6.92 (t, 1H, J=7.4 Hz), 6.84 (d, 1H, J=8.4 Hz), 3.99 (dd, 1H, J=8.8 Hz, J=5.7 Hz), 3.87 (d, 1H, J=13.3 Hz), 3.76 (s, 3H), 3.75 (d, 1H, J=13.3 Hz), 3.56 (t, 2H, J=6.5 Hz), 3.10 (dd, 1H, J=11.2 Hz, J=9.1 Hz), 2.75 (dd, 1H, J=11.3 Hz, J=5.7 Hz), 5H), 1.75-0.88 (br.m, 18H) ppm.

$^{13}$C NMR (CDCl$_3$, 62.90 MHz) δ 157.5, 141.5, 129.9, 128.2, 128.1, 127.9, 126.8, 120.2, 110.0, 62.4, 56.8, 54.9, 50.6, 49.2, 45.9, 33.0, 32.8, 30.4, 29.8, 27.0, 26.6, 26.2, 26.1, 25.6 ppm.

IR (neat) λ 3000 (w), 2940, 2870, 1620 (w), 1500 (w), 1460, 1200 (br), 1040 (br) cm$^{-1}$.

Mass spectrum (dihydrochloride salt) FAB 4397 (P+$^1$).

I claim:

1. A compound of the formula

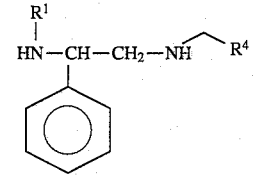

wherein $R^1$ is $(C_1-C_8)$ alkyl or $(C_3-C_8)$ cycloalkyl and $R^4$ is a monosubstituted or disubstituted aryl group that is substituted at the C-2 position with analkoxy group or substituted at the C-5 position with an alkyl, alkoxy or trihaloalkoxy group, or substituted in such manner at both the C-2 and C-5 positions, or a pharmaceutically acceptable salt of such compound.

2. A compound according to claim 1, wherein said compound is selected from:

1-N-cyclohexyl-1-phenyl-2-N'-[(2 -methoxyphenyl)methyl]-1,2-ethanediamine;

1-N-cyclohexyl-1-phenyl-2-N'-[(2 -methoxy-5trifluoromethoxyphenyl)methyl]-1,2-ethanediamine;

1-N-methyl-1-phenyl-2-N'-[(2 -methoxyphenyl)methyl]-1,2-ethanediamine;

1-N-cyclopentyl-1-phenyl-2-N'-[(2-methoxyphenyl)methyl]-1,2-ethanediamine;

1-N-propyl-1-phenyl-2-N'-[(2 -methoxyphenyl)methyl]-1,2-ethanediamine;

1-N-cyclooctyl-1-phenyl-2-N'-[(2-methoxyphenyl)methyl]-1,2-ethanediamine;

1-N-cyclobutyl-1-phenyl-2-N'-[(2 -methoxyphenyl)methyl]-1,2-ethanediamine;

1-N-(1,1-dimethylethyl)-1-phenyl-2 -N'-[(2-methoxyphenyl)methyl]-1,2-ethanediamine;

1-N-cyclopropyl-1-phenyl-2-N'-[(2-methoxyphenyl)methyl]-1,2-ethanediamine;

1-N-isopropyl-1-phenyl-2-N'-[(2-methoxyphenyl)methyl]-1,2-ethanediamine;

1-N-cyclohexyl-1-phenyl-2-N'-[(2-methoxy-5-tertbutylphenyl)methyl]-1,2-ethanediamine and;

1-N-cyclohexyl-1-phenyl-2-N'-[(2-methoxy-5-isopropylphenyl)methyl]-1,2-ethanediamine.

3. A compound according to claim 1, wherein said compound is selected from:

1-N-cyclohexyl-1-phenyl-2-N'-[(2-methoxy-5-trifluoromethoxyphenyl)methyl]-1,2-ethanediamine;

1-N-(1,1-dimethylethyl)-1-phenyl-2-N'-[(2-methoxyphenyl)methyl]-1,2-ethanediamine dihydrochloride;

1-N-cyclopropyl-1-phenyl-2-N'-[(2-methoxyphenyl)methyl]-1,2-ethanediamine dihydrochloride;

1-N-isopropyl-1-phenyl-2-N'-[(2-methoxyphenyl)methyl]-1,2-ethanediamine dihydrochloride.

4. A pharmaceutical composition for treating or preventing a condition selected from the group consisting of inflammatory diseases, anxiety, colitis, depression or dysthymic disorders, psychosis, pain, allergies, chronic obstructive airways disease, hypersensitivity disorders, vasospastic diseases, fibrosing and collagen diseases, reflex sympathetic dystrophy, addiction disorders, stress related somatic disorders, peripheral neuropathy, neuralgia, neuropathological disorders, disorders related to immune enhancement or suppression and rheumatic diseases in a mammal, comprising an amount of a compound according to claim 1 effective in preventing or treating such condition and a pharmaceutically acceptable carrier.

5. A method of treating or preventing a condition selected from the group consisting of inflammatory diseases anxiety, colitis, depression or dysthymic disorders, psychosis, pain, allergies, chronic obstructive airways disease, hypersensitivity disorders, vasospastic diseases, fibrosing and collagen diseases, reflex sympathetic dystrophy, addiction disorders, stress related somatic disorders, peripheral neuropathy, neuralgia, neuropathological disorders, disorders related to immune enhancement or suppression and rheumatic diseases in a mammal, comprising administering to a mammal in need of such treatment or prevention an amount of a compound according to claim 1 effective in preventing or treating such condition.

6. A pharmaceutical composition for antagonizing the effects of substance P at its receptor site in a mammal, comprising a substance P receptor antagonizing effective amount of a compound according to claim 1 and a pharmaceutically acceptable carrier.

7. A method of antagonizing the effects of substance P at its receptor site in a mammal, comprising administering to said mammal a substance P receptor antagonizing effective amount of a compound according to claim 1.

8. A pharmaceutical composition for treating or preventing a condition in a mammal, the treatment or prevention of which is effected or facilitated by a decrease in substance P mediated neurotransmission, comprising an amount of a compound according to claim 1 effective in antagonizing the effect of substance P at its receptor site and a pharmaceutically acceptable carrier.

9. A method of treating or preventing a condition in a mammal, the treatment or prevention of which is effected or facilitated by a decrease in substance P mediated neurotransmission, comprising administering to a mammal in need of such treatment or prevention an amount of a compound according to claim 1, or a pharmaceutically acceptable salt thereof, effective in antagonizing the effect of substance P at its receptor site.

10. A pharmaceutical composition for treating or preventing a condition in a mammal, the treatment or prevention of which is effectedor facilitated by a decrease in substance P mediated neurotransmission, comprising an amount of a compound according to claim 1, or a pharmaceutically acceptable salt thereof, effective in treating or preventing such condition and a pharmaceutically acceptable carrier.

11. A method of treating or preventing a condition in mammal, the treatment or prevention of which is effected or facilitated by a decrease in substance P mediated neurotransmission, comprising administering to a mammal in need of such treatment or prevention an amount of a compound according to claim 1 effective in treating or preventing such condition.

* * * * *